(12) United States Patent
Donnet-Hughes et al.

(10) Patent No.: US 8,377,430 B2
(45) Date of Patent: Feb. 19, 2013

(54) INFANT FORMULA WITH PROBIOTICS

(75) Inventors: Anne Donnet-Hughes, Saint-Legier (CH); Eduardo Schiffrin, Crissier (CH); Ferdinand Haschke, Frankfurt am Main (DE); Marie-Claire Fichot, La Tour de Peilz (CH); Karl-Josef Huber-Haag, Pully (CH)

(73) Assignee: Nestec S.A., Vevey (CH)

( * ) Notice: Subject to any disclaimer, the term of this patent is extended or adjusted under 35 U.S.C. 154(b) by 1134 days.

(21) Appl. No.: 11/911,323

(22) PCT Filed: Apr. 10, 2006

(86) PCT No.: PCT/EP2006/061491
§ 371 (c)(1),
(2), (4) Date: Aug. 11, 2008

(87) PCT Pub. No.: WO2006/108824
PCT Pub. Date: Oct. 19, 2006

(65) Prior Publication Data
US 2009/0304655 A1 Dec. 10, 2009

(30) Foreign Application Priority Data
Apr. 13, 2005 (EP) .................... 05102896

(51) Int. Cl.
*A01N 63/00* (2006.01)
*A01N 65/00* (2009.01)
*C12N 1/00* (2006.01)
*C12N 1/12* (2006.01)
*C12N 1/20* (2006.01)

(52) U.S. Cl. .............. 424/93.1; 424/93.3; 424/93.4; 424/93.44; 424/93.45; 424/93.48; 435/243; 435/252.1; 435/252.4; 435/252.9; 435/253.4; 435/822; 435/853

(58) Field of Classification Search .......... None
See application file for complete search history.

(56) References Cited

U.S. PATENT DOCUMENTS 5,902,578 A * 5/1999 Halpin-Dohnalek et al. ................. 424/93.3

FOREIGN PATENT DOCUMENTS

| EP | 0 199 535 | 10/1986 |
|---|---|---|
| EP | 0 577 903 | 1/1994 |
| EP | 0 768 375 | 4/1997 |
| EP | 0 880 902 | 2/1998 |
| WO | WO 97/00078 | 1/1997 |
| WO | WO 00/53200 | 9/2000 |
| WO | WO 01/11990 | 2/2001 |
| WO | WO 01/22837 | 4/2001 |
| WO | WO 2004/032639 | 4/2004 |
| WO | WO 2004/112507 | 12/2004 |
| WO | WO 2004/112508 | 12/2004 |
| WO | WO 2004/112509 | 12/2004 |

OTHER PUBLICATIONS

Agostoni, et al., "Probiotic Bacteria in Dietetic Products for Infants: A Commentary by the Espghan Committee on Nutrition," Journal of Pediatric Gastroenterology and Nutrition, vol. 38, pp. 365-374 (2004).

Martin, R. et al., "Human Milk is a Source of Lactic Acid Bacteria for the Infant Gut," The Journal of Pediatrics, vol. 143, pp. 754-758, Dec. 2003.

Salminen, S. et al., "Probiotics: How Should They Be Defined?" Trends in Food Science & Technology, vol. 10, pp. 107-110 (1999).

* cited by examiner

Primary Examiner — Debbie K Ware
(74) Attorney, Agent, or Firm — K&L Gates LLP

(57) ABSTRACT

The invention relates to an infant formula comprising a source of protein in an amount of not more than 2.0 g/100 kcal, a source of lipids, a source of carbohydrate and a probiotic wherein the probiotic is present in an amount equivalent to between $10^2$ and $10^5$ cfu/g of dry formula. The invention further extends to the use of such an infant formula to modulate the immune system of a neonatal infant to promote the development in the first few weeks of the life of the infant of a beneficial intestinal microbiota comparable with that found in breast fed babies as well as to promote the maturation of the immune system of a neonatal infant in the first few weeks of life.

22 Claims, No Drawings

INFANT FORMULA WITH PROBIOTICS

This application is a filing under 37 U.S.C. 371, of International Application No. PCT/EP2006/061491, filed Apr. 10, 2006.

This invention relates to an infant formula with probiotics.

Mother's milk is recommended for all infants. However, in some cases breast feeding is inadequate or unsuccessful for medical reasons or the mother chooses not to breast feed. Infant formulae have been developed for these situations.

In the recent past, certain strains of bacteria have attracted considerable attention because they have been found to exhibit valuable properties for man if ingested. In particular, specific strains of the genera *Lactobacilli* and *Bifidobacteria* have been found to be able to colonise the intestinal mucosa, to reduce the capability of pathogenic bacteria to adhere to the intestinal epithelium, to have immunomodulatory effects and to assist in the maintenance of well-being. Such bacteria are sometimes called probiotics.

Extensive studies have been carried out to identify new probiotic strains. For example, EP 0 199 535, EP 0 768 375, WO 97/00078, EP 0 577 903 and WO 00/53200 disclose specific strains of *Lactobacilli* and *Bifidobacteria* and their beneficial effects.

As far as infants specifically are concerned, immediately before birth, the gastro-intestinal tract of a baby is thought to be sterile. During the process of birth, it encounters bacteria from the digestive tract and skin of the mother and starts to become colonised. Large differences exist with respect to the composition of the gut microbiota in response to the infant's feeding. The fecal flora of breast-fed infants includes appreciable populations of *Bifidobacteria* with some *Lactobacillus* species, whereas formula-fed infants have more complex microbiota, with *Bifidobacteria, Bacteroides, Clostridia* and *Streptococci* all usually present. After weaning at about 2 years of age, a pattern of gut microbiota that resembles the adult pattern becomes established.

For this reason, it has been proposed to add probiotics to infant formulae to encourage gut colonization to take place and to promote colonization with the "good" bacteria—species of *Bifidobacteria* and *Lactobacilli*—rather than the harmful bacteria—pathogens such as clostridia, etc. Typically a minimum of $10^7$ cfu/g of formula is added although generally larger amounts are preferred, for example up to $10^{12}$ cfu/g of formula.

More recently, some concerns have been expressed about the addition of probiotic bacteria to infant formula which is intended as the sole source of nutrition for infants in the first six months of life. These concerns were summarized in the medical position paper from the ESPGHAN Committee on Nutrition entitled "Probiotic Bacteria in Dietetic Products for Infants" (Journal of Paediatric Gastroenterology and Nutrition, 38:365-374).

Meanwhile, research into the components of human milk is advancing rapidly. It had always been supposed that human breast milk was sterile. However, very recently and as described for example by Martin et al in their article "Human milk is a source of lactic acid bacteria for the infant gut" (J. Pediatr. 2003; 143: 754-8) a number of bacterial strains have been isolated from human breast milk. It is not, at the moment, possible to state conclusively that such bacteria are capable of reproducing or, at least, that all strains identified are so capable. Nevertheless, it is thought that these bacteria and bacterial fragments must be present in human milk for a specific purpose or purposes.

For the benefit of infants that will not be completely breast fed, there is a continuing need to develop infant formulae which will replicate human milk as far as possible, both in terms of its nutritional and its bioactive properties.

SUMMARY OF THE INVENTION

The present inventors have surprisingly discovered that as investigations into the presence of bacteria and bacterial fragments in human colostrum and human milk continue, a common denominator is starting to emerge, namely that whatever specific strains are found, their concentration appears to be much lower than the concentrations previously proposed for addition to infant formulae.

Accordingly, the present invention provides an infant formula comprising a source of protein in an amount of not more than 2.0 g/100 kcal, a source of lipids, a source of carbohydrate and a probiotic wherein the probiotic is present in an amount equivalent to $10^2$ and $10^5$ cfu/g of dry formula.

The invention also extends to the use of a probiotic in the manufacture of an infant formula for promoting the maturation of the immune system of a neonatal infant in the first few weeks of the life of the infant wherein the probiotic is present in an amount equivalent to $10^2$ and $10^5$ cfu/g of dry formula.

The invention further extends to the use of a probiotic in the manufacture of an infant formula for modulating the immune system of a neonatal infant to promote in the first few weeks of the life of the infant the development of a beneficial intestinal microbiota comparable with that found in breast fed babies wherein the probiotic is present in the formula in an amount equivalent to $10^2$ and $10^5$ cfu/g of dry formula.

In a further aspect, the invention extends to a method for promoting the maturation of the immune system of a neonatal infant in need thereof in the first few weeks of the life of the infant which comprises administering to the infant a therapeutic amount of an infant formula containing a probiotic in an amount equivalent to between $10^2$ and $10^5$ cfu/g of dry formula.

In a last aspect, the invention extends to a method for modulating the immune system of a neonatal infant in need thereof to promote in the first few weeks of the life of the infant the development of a beneficial intestinal microbiota comparable with that found in breast fed babies which comprises administering to the infant a therapeutic amount of an infant formula containing a probiotic in an amount equivalent to between $10^2$ and $10^5$ cfu/g of dry formula.

Without wishing to be bound by theory, the present inventors believe that it is possible that the introduction of relatively low levels of probiotic bacteria into the digestive tract of a neonatal infant in some way promotes maturation of the immune system of the infant and prepares or primes the immune system of the infant to suppress any tendency to mount an inflammatory response against colonization by beneficial organisms and thus favour the development of a beneficial gut microbiota over the next few weeks and months of life whilst maintaining a competent immune defense against colonization by pathogens. It is possible that this effect, albeit still an immunomodulatory effect, is physiologically different from the effect on the immune system of the far larger quantities of probiotic bacteria that have been conventionally added to infant formula and, indeed, to other food products for human consumption. It is even possible that the present invention may offer the possibility to "re-train" the immune system of older children and adults who suffer from conditions associated with an inability of the immune system to recognise beneficial commensal bacteria such as *Bifidobac-*

*teria* as a result of which the immune system attacks such bacteria in the same way as it attacks pathogenic bacteria.

DETAILED DESCRIPTION OF THE INVENTION

In the present specification, the following words are given a definition that must be taken into account when reading and interpreting the description, examples and claims.

The following definitions appear in Article 1.2 of the European Commission Directive 91/321/EEC of 14 May 1991 on infant formulae and follow-on formulae and are adopted in the present specification:—

"Infant": child under the age of 12 months;

"Infant formula": foodstuff intended for the complete nutrition of infants during the first six months of life.

The expression "beneficial intestinal microbiota comparable with that found in breast fed babies" means an intestinal microbiota dominated by appreciable populations of *Bifidobacterium* and *Lactobacillus* species to the exclusion of appreciable populations of such species as *Bacteroides, Clostridia* and *Streptococci*.

"Probiotics": probiotics are defined as microbial cell preparations or components of microbial cells with a beneficial effect on the health or well-being of the host. (Salminen S, Ouwehand A. Benno Y. et al "Probiotics: how should they be defined" Trend Food Sci. Technol. 1999:10 107-10).

The expression "the first few weeks of the life of an infant" means the first two months of life.

The probiotic is present in the formula in an amount equivalent to between $10^2$ and $10^5$ cfu/g of dry formula. This expression includes the possibilities that the bacteria are live, inactivated or dead or even present as fragments such as DNA or cell wall materials. In other words, the quantity of bacteria which the formula contains is expressed in terms of the colony forming ability of that quantity of bacteria as if all the bacteria were live irrespective of whether they are, in fact, live, inactivated or dead, fragmented or a mixture of any or all of these states. Preferably the probiotic is present in an amount equivalent to between $10^2$ to $10^4$ cfu/g of dry formula, even more preferably in an amount equivalent to between $10^3$ and $10^4$ cfu/g of dry formula.

The infant formula according to the present invention contains a protein source in an amount of not more than 2.0 g/100 kcal, preferably 1.8 to 2.0 g/100 kcal. The type of protein is not believed to be critical to the present invention provided that the minimum requirements for essential amino acid content are met and satisfactory growth is ensured although it is preferred that over 50% by weight of the protein source is whey. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in whatever proportions are desired.

Preferably, however, the protein source is based on modified sweet whey. Sweet whey is a readily available by-product of cheese making and is frequently used in the manufacture of infant formulas based on cows' milk. However, sweet whey includes a component which is undesirably rich in threonine and poor in tryptophan called caseino-glyco-macropeptide (CGMP). Removal of the CGMP from sweet whey results in a protein with a threonine content closer to that of human milk. This modified sweet whey can then be supplemented with those amino acids in respect of which it has a low content (principally histidine and tryptophan). A process for removing CGMP from sweet whey is described in EP 880902 and an infant formula based on this modified sweet whey is described in WO 01/11990. Using modified sweet whey as the principal protein in the protein source enables all essential amino acids to be provided at a protein content between 1.8 and 2.0 g/100 kcal. Such protein sources have been shown in animal and human studies to have a protein efficiency ratio, nitrogen digestibility, biological value and net protein utilisation comparable to standard whey-adapted protein sources with a much higher protein content per 100 kcal and to result in satisfactory growth despite their reduced protein content. If modified sweet whey is used as the protein source, it is preferably supplemented by free histidine in an amount of from 0.1 to 1.5% by weight of the protein source.

The proteins may be intact or hydrolysed or a mixture of intact and hydrolysed proteins. It may be desirable to supply partially hydrolysed proteins (degree of hydrolysis between 2 and 20%), for example for infants believed to be at risk of developing cows' milk allergy. If hydrolysed proteins are required, the hydrolysis process may be carried out as desired and as is known in the art. For example, a whey protein hydrolysate may be prepared by enzymatically hydrolysing the whey fraction in one or more steps. For an extensively hydrolysed protein, the whey proteins may be subjected to triple hydrolysis using Alcalase 2.4 L (EC 940459), then Neutrase 0.5 L (obtainable from Novo Nordisk Ferment AG) and then pancreatin at 55° C. Alternatively, for a less hydrolysed protein, the whey may be subjected to double hydrolysis using NOVOZYMES and then pancreatin. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

The infant formula according to the present invention contains a carbohydrate source. Any carbohydrate source conventionally found in infant formulae such as lactose, saccharose, maltodextrin, starch and mixtures thereof may be used although the preferred source of carbohydrates is lactose. Preferably the carbohydrate sources contribute between 35 and 65% of the total energy of the formula.

The infant formula according to the present invention contains a source of lipids. The lipid source may be any lipid or fat which is suitable for use in infant formulas. Preferred fat sources include palm olein, high oleic sunflower oil and high oleic safflower oil. The essential fatty acids linoleic and α-linolenic acid may also be added as may small amounts of oils containing high quantities of preformed arachidonic acid and docosahexaenoic acid such as fish oils or microbial oils. In total, the fat content is preferably such as to contribute between 30 to 55% of the total energy of the formula. The fat source preferably has a ratio of n−6 to n−3 fatty acids of about 5:1 to about 15:1; for example about 8:1 to about 10:1.

The infant formula will also contain all vitamins and minerals understood to be essential in the daily diet and in nutritionally significant amounts. Minimum requirements have been established for certain vitamins and minerals. Examples of minerals, vitamins and other nutrients optionally present in the infant formula include vitamin A, vitamin $B_1$, vitamin $B_2$, vitamin $B_6$, vitamin $B_{12}$, vitamin E, vitamin K, vitamin C, vitamin D, folic acid, inositol, niacin, biotin, pantothenic acid, choline, calcium, phosphorous, iodine, iron, magnesium, copper, zinc, manganese, chloride, potassium, sodium, selenium, chromium, molybdenum, taurine, and L-carnitine. Minerals are usually added in salt form. The presence and amounts of specific minerals and other vitamins will vary depending on the intended infant population.

If necessary, the infant formula may contain emulsifiers and stabilisers such as soy lecithin, citric acid esters of mono- and di-glycerides, and the like. This is especially the case if the formula is provided in liquid form.

The infant formula may optionally contain other substances which may have a beneficial effect such as fibres, lactoferrin, nucleotides, nucleosides, and the like.

The probiotic may be selected from any strain which satisfies the definition of a probiotic given above. It may be for example a *Lactobacillus*, a *Bifidobacterium*, a *Streptococcus*, a *Lactococcus*, a *Leuconostoc*, an *Enterobacteriaceae* or an *Enterococcus*. Examples of preferred *Lactobacillus* species are *Lactobacillus rhamnosus* and *Lactobacillus paracasei*. Particularly preferred strains are *Lactobacillus rhamnosus* ATCC 53103 obtainable from Valio Oy of Finland under the trade mark LGG, *Lactobacillus rhamnosus* CGMCC 1.3724 and *Lactobacillus paracasei* CNCM I-2116. Examples of preferred *Bifidobacterium* species are *Bifidobacterium lactis*, *Bifidobacterium breve*, *Bifidobacterium longum* and *Bifidobacterium animalis*. Particularly preferred strains are the strain of *Bifidobacterium* lactis sold by the Christian Hansen company of Denmark under the trade mark BB12, *Bifidobacterium lactis* CNCM I-3446, *Bifidobacterium longum* ATCC BAA-999 obtainable from Morinaga Milk Industry Co. Ltd. of Japan under the trade mark BB536 and *Bifidobacterium breve* obtainable from Rhodia under the trade mark Bb-03. Examples of preferred *Streptococcus* species are *Streptococcus thermophilus* and *Streptococcus salivarius*. A particularly preferred strain is the strain of *Streptococcus thermophilus* sold by the Christian Hansen company under the trade mark TH4. An example of a preferred *Lactococcus* species is *Lactococcus lactis*. An example of a preferred *Leuconostoc* species is *Leuconostoc lactis*. An example of a preferred *Enterococcus* species is *Enterococcusfaecium*.

Preferably at least two different probiotics are present, provided that the upper limit of $10^5$ cfu/g of dry formula is respected. One particularly preferred combination is a *Lactobacillus* such as a *Lactobacillus rhamnosus* or *Lactobacillus paracasei* species for example and a *Bifidobacterium* such as a *Bifidobacterium lactis*, *Bifidobacterium longum*, *Bifidobacterium breve* or *Bifidobacterium animalis* species for example. Examples of such combinations of strains are *Bifidobacterium longum* ATCC BAA-999 with *Lactobacillus rhamnosus* ATCC 53103, *Lactobacillus paracasei* CNCM 1-2116 or *Lactobacillus rhamnosus* CGMCC 1.3724. Another particularly preferred combination is two *Bifidobacterium* strains. One example of such a combination is *Bifidobacterium longum* ATCC BAA-999 with *Bifidobacterium lactis* CNCM I-3446.

As noted above, the quantity of the probiotic or probiotics used should not exceed the equivalent of $10^5$ cfu/g of dry product and is preferably equivalent to between $10^3$ and $10^4$ cfu/g. The strains may be live or inactivated or dead or fragmented when added to the formula or a mix. Alternatively a mixture of bacteria in any or all of these different states may be used.

The infant formula may be prepared in any suitable manner. For example, an infant formula may be prepared by blending together the protein source, the carbohydrate source, and the fat source in appropriate proportions. If used, the emulsifiers may be included in the blend. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture.

The liquid mixture may then be thermally treated to reduce bacterial loads. For example, the liquid mixture may be rapidly heated to a temperature in the range of about 80° C. to about 110° C. for about 5 seconds to about 5 minutes. This may be carried out by steam injection or by heat exchanger; for example a plate heat exchanger.

The liquid mixture may then be cooled to about 60° C. to about 85° C.; for example by flash cooling. The liquid mixture may then be homogenised; for example in two stages at about 7 MPa to about 40 MPa in the first stage and about 2 MPa to about 14 MPa in the second stage. The homogenised mixture may then be further cooled to add any heat sensitive components; such as vitamins and minerals. The pH and solids content of the homogenised mixture is conveniently standardised at this point.

The homogenised mixture is transferred to a suitable drying apparatus such as a spray drier or freeze drier and converted to powder. The powder should have a moisture content of less than about 5% by weight.

The selected probiotic(s) may be cultured according to any suitable method and prepared for addition to the infant formula by freeze-drying or spray-drying for example. Alternatively, bacterial preparations can be bought from specialist suppliers such as Christian Hansen and Morinaga already prepared in a suitable form for addition to food products such as infant formula.

Example 1

An example of the composition of an infant formula according to the present invention is given below. This composition is given by way of illustration only.

| Nutrient | per 100 kcal | per litre |
| --- | --- | --- |
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (μg) | 8 | 50 |
| Se (μg) | 2 | 13 |
| Vitamin A (μg RE) | 105 | 700 |
| Vitamin D (μg) | 1.5 | 10 |
| Vitamin E (mg TE) | 0.8 | 5.4 |
| Vitamin K1 (μg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (μg) | 9 | 60 |
| Pantothenic acid (mg) | 0.45 | 3 |
| Vitamin B12 (μg) | 0.3 | 2 |
| Biotin (μg) | 2.2 | 15 |
| Choline (mg) | 10 | 67 |
| Fe (mg) | 1.2 | 8 |
| I (μg) | 15 | 100 |
| Cu (mg) | 0.06 | 0.4 |
| Zn (mg) | 0.75 | 5 |
| *L. rhamnosus* ATCC 53103 | $10^3$ cfu/g of powder, live bacteria | |
| *B. longum* BB 536 | $10^2$ cfu/g of powder, live bacteria | |

Example 2

The following animal study describes an investigation evaluating the effect of administration of probiotics according to the invention on the maturation of the immune system of neonatal mice pups.

30 pregnant germ-free mice are randomized into five groups. The pups are allocated to one of five groups (n=24 to 28 pups per group). All pups from a single mother go to the same group. Four of the groups receive probiotics alone or in combination with bacteria from normal murine microbiota (enterobacteria) as follows: —
Group 1: Controls (placebo)
Group 2: Probiotics ($10^4$ cfu)
Group 3: Probiotics plus murine flora ($10^4$ cfu probiotics and $10^3$ cfu enterobacteria)
Group 4: Probiotics ($10^8$ cfu)
Group 5: Probiotics plus murine flora ($10^8$ cfu probiotics and $10^3$ cfu enterobacteria)

This experimental setting is used to test the following probiotics: *Lactobacillus rhamnosus* ATCC 53103, *Bifidobacterium longum* ATCC BAA-999, *Lactobacillus paracasei* CNCM 1-2116 and combinations of *Lactobacillus rhamnosus* ATCC 53103 and *Bifidobacterium longum* ATCC BAA-999 and *Lactobacillus paracasei* CNCM I-2116 and *Bifidobacterium longum* ATCC BAA-999.

The mothers and the pups receive a classical sterile diet. They are kept in isolators until 10 days after birth and have free access to food and water.

The pups in groups 2 to 5 receive the bacteria concentrated in one drop of PBS (corresponding to about 10 µl) whilst the pups in the control group receive the PBS alone. The PBS with and without bacteria according to the group is administered orally on a daily basis to the pups from 7 days after birth until weaning. The pups and their mothers are transferred to a conventional environment 10 days after birth.

The pups in each group are divided into four sub-sets. One sub-set of pups from each group is sacrificed 7 days after birth to determine the different markers at the baseline. Two further sub-sets of pups from each group are sacrificed at Days 10 and 14 of age respectively. Pups in the remaining sub-set in each group are immunized with systemic vaccine (subcutaneous administration of tetanus toxoid vaccine 0.125 Lf/mouse in aluminium hydroxide) at weaning (Day 21 of age). The immune response to the vaccine is followed weekly for three weeks and then the remaining pups are sacrificed. Blood (for the detection of IgG antibodies) and feces (for assessment of microbiota and detection of IgA antibodies) are taken from all pups at Day 21, Day 28 and Day 35 of age. Post mortem blood and tissue samples (spleen, intestine, liver, mesenteric lymph nodes and mammary glands) are taken under sterile conditions.

The following outcome variables are measured:—

Immune maturation assessed by evaluation of histology and immuno-histochemistry of intestinal tissue and determination of proportion and phenotype of immune cells as well as subsets and levels of fecal IgA;

Immune response to vaccination by specific IgG and cytokine levels in the blood using ELISA techniques;

Analysis of endogeneous microbiota, counting and determination of bacteria in feces.

The invention claimed is:

1. An infant formula comprising a source of protein ranging from 1.8 to 2.0 g/100 kcal, a source of lipids, a source of carbohydrate, and at least one probiotic wherein the total amount of the at least one probiotic is between $10^2$ to $10^5$ cfu/g of dry formula.

2. An infant formula according to claim 1, wherein over 50% by weight of the protein source is whey protein.

3. An infant formula according to claim 1, wherein the at least one probiotic is selected from the group consisting of a *Lactobacillus* strain, a *Bifidobacterium* strain, a *Streptococcus* strain, a *Lactococcus* strain, a *Leuconostoc* strain, an *Enterobacteriaceae* strain and an *Enterococcus* strain.

4. An infant formula according to claim 3 wherein the *Lactobacillus* strain is a species selected from the group consisting of *Lactobacillus rhamnosus* and *Lactobacillus paracasei*.

5. An infant formula according to claim 4 wherein the *Lactobacillus* strain is selected from the group consisting of *Lactobacillus rhamnosus* ATCC 53103, *Lactobacillus paracasei* CNCM 1-2116 and *Lactobacillus rhamnosus* CGMCC 1.3724.

6. An infant formula according to claim 3 wherein the *Bifidobacterium* strain is a species selected from the group consisting of *Bifidobacterium lactis*, *Bifidobacterium longum*, *Bifidobacterium breve* and *Bifidobacterium animalis*.

7. An infant formula according to claim 6 wherein the *Bifidobacterium* strain is selected from the group consisting of *Bifidobacterium longum* ATCC BAA-999 and *Bifidobacterium lactis* CNCM 1-3446.

8. An infant formula according to claim 1 comprising at least two different probiotics.

9. An infant formula according to claim 8 comprising a *Lactobacillus* strain and a *Bifidobacterium* strain.

10. An infant formula according to claim 9 wherein the *Lactobacillus* strain is selected from the group consisting of *Lactobacillus rhamnosus* ATCC 53103 and *Lactobacillus paracasei* CNCM 1-2116, and the *Bifidobacterium* strain is selected from the group consisting of *Bifidobacterium longum* ATCC BAA-999 and *Bifidobacterium lactis* CNCM 1-3446.

11. An infant formula according to claim 1 wherein the total amount of the at least one probiotic is between $10^3$ to $10^4$ cfu/g of dry formula.

12. A method of manufacturing an infant formula for modulating the immune system of a neonatal infant, the method comprising adding protein and at least one probiotic, such that the protein amount ranges from 1.8 to 2.0 g/100 kcal, and the at least one probiotic is present in an amount of $10^2$ to $10^5$ cfu/g of dry formula.

13. A method of promoting maturation of the immune system of a neonatal infant in the first few weeks of the life of the infant, the method comprising administering to the neonatal infant in need of same an infant formula comprising protein ranging from 1.8 to 2.0 g/100 kcal and at least one probiotic that is present in the infant formula in an amount of $10^2$ to $10^5$ cfu/g of dry formula.

14. The method according to claim 13, wherein the infant formula further comprises a source of lipids and a source of carbohydrate.

15. The method according to claim 13, wherein over 50% by weight of the protein source is whey protein.

16. The method according to claim 13, wherein the at least one probiotic is selected from the group consisting of a *Lactobacillus* strain, a *Bifidobacterium* strain, a *Streptococcus* strain, a *Lactococcus* strain, a *Leuconostoc* strain, an *Enterobacteriaceae* strain and an *Enterococcus* strain.

17. The method according to claim 13, wherein the infant formula comprises at least two different probiotics.

18. A method for modulating the immune system of a neonatal infant to promote the development in the first few weeks of the life of the infant a beneficial intestinal microbiota comparable with that found in breast fed babies, the method comprising administering to the infant in need of same an infant formula comprising protein ranging from 1.8 to 2.0 g/100 kcal and at least one probiotic that is present in the infant formula in an amount of $10^2$ to $10^5$ cfu/g of dry formula.

19. The method according to claim 18, wherein the infant formula further comprises a source of lipids and a source of carbohydrate.

20. The method according to claim 18, wherein over 50% by weight of the protein is whey protein.

21. The method according to claim 18, wherein the at least one probiotic is selected from the group consisting of a *Lactobacillus* strain, a *Bifidobacterium* strain, a *Streptococcus* strain, a *Lactococcus* strain, a *Leuconostoc* strain, an *Enterobacteriaceae* strain and an *Enterococcus* strain.

22. The method according to claim 18, wherein the infant formula comprises at least two different probiotics.

* * * * *